US010443085B2

(12) United States Patent
Nakamura et al.

(10) Patent No.: US 10,443,085 B2
(45) Date of Patent: Oct. 15, 2019

(54) METHOD FOR DETECTING NUCLEIC ACID AND NUCLEIC ACID DETECTION KIT

(71) Applicant: TORAY INDUSTRIES, INC., Tokyo (JP)

(72) Inventors: Fumio Nakamura, Kamakura (JP); Yoji Ueda, Kamakura (JP); Takafumi Arike, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 110 days.

(21) Appl. No.: 14/409,855

(22) PCT Filed: Jun. 19, 2013

(86) PCT No.: PCT/JP2013/066799
§ 371 (c)(1),
(2) Date: Dec. 19, 2014

(87) PCT Pub. No.: WO2013/191197
PCT Pub. Date: Dec. 27, 2013

(65) Prior Publication Data

US 2015/0322483 A1 Nov. 12, 2015

(30) Foreign Application Priority Data

Jun. 20, 2012 (JP) ................................ 2012-138336

(51) Int. Cl.
*G01N 33/00* (2006.01)
*C12Q 1/6806* (2018.01)
*C12Q 1/6825* (2018.01)
*C12Q 1/6834* (2018.01)

(52) U.S. Cl.
CPC ......... *C12Q 1/6806* (2013.01); *C12Q 1/6825* (2013.01); *C12Q 1/6834* (2013.01)

(58) Field of Classification Search
None
See application file for complete search history.

(56) References Cited

U.S. PATENT DOCUMENTS 5,646,019 A 7/1997 Nielson et al.
5,660,984 A * 8/1997 Davis ....................... B01J 41/20 210/323.2
5,846,717 A 12/1998 Brow et al.
5,906,918 A * 5/1999 Box ..................... C12Q 1/6869 435/6.14
5,994,079 A * 11/1999 De La Rosa ........ C12Q 1/6804 435/6.1
2003/0017465 A1 1/2003 Kay
2003/0175776 A1 9/2003 Nakao et al.
2004/0072150 A1* 4/2004 Shyamala .............. C12Q 1/703 435/5
2004/0106108 A1* 6/2004 Grenier ................ C12Q 1/6823 435/6.18
2004/0180345 A1 9/2004 Erikson et al.
2008/0242560 A1* 10/2008 Gunderson .......... B01J 19/0046 506/26
2011/0297545 A1* 12/2011 Latham ............ G01N 27/44739 204/464

FOREIGN PATENT DOCUMENTS

EP 1526176 A2 * 4/2005 ......... C12N 15/1017
EP 1526176 A2 * 4/2005 ......... C12N 15/1017
JP 2002-515737 A 5/2002
JP 2002-535998 A 10/2002
JP 2003-52383 A 2/2003
JP 2003-514227 A 4/2003
JP 2003-265180 A 9/2003
JP 2010-029174 A 2/2010
JP 2011-152054 A 8/2011
JP 2011-188837 A 9/2011
WO 2001/035100 A2 5/2001

OTHER PUBLICATIONS

"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Mammal," (Wikipedia.com; accessed Sep. 22, 2011).*
"Murinae," (Wikipedia.com, accessed Mar. 18, 2013).*
"List of sequenced bacterial genomes" (Wikipedia.com; accessed Jan. 24, 2014).*
"Viruses", Wikipedia.com, accessed Nov. 24, 2012. (Year: 2012).*
"How many species of bacteria are there", wisegeek.com; accessed Jan. 21, 2014. (Year: 2014).*

(Continued)

*Primary Examiner* — Bradley L. Sisson
(74) *Attorney, Agent, or Firm* — Birch, Stewart, Kolasch & Birch, LLP

(57) ABSTRACT

Disclosed is a method for detecting a nucleic acid using a substance that suppresses, in the labeling step of the post-staining method, detachment of a target nucleic acid that has once hybridized with a capture probe immobilized on a support, which method enables detection of the target nucleic acid with a sensitivity equivalent to or higher than that achieved by a method using sodium ion even in cases where the substance is used at a lower concentration. The method for detecting a nucleic acid comprises the steps of: (1) hybridizing a capture probe with a target nucleic acid to form a double-stranded nucleic acid; bringing the formed double-stranded nucleic acid into contact with a solution containing a labeling substance and a divalent metal cation at a concentration of not less than 10 mM to introduce the labeling substance into the double-stranded nucleic acid; and detecting the labeling substance introduced into the double-stranded nucleic acid.

3 Claims, No Drawings

Specification includes a Sequence Listing.

(56) References Cited

OTHER PUBLICATIONS

"Fungi," Wikipedia.com; accessed Jun. 3, 2013. (Year: 2013).*
"Mammal," Wikipedia.com; accessed Sep. 22, 2011. (Year: 2011).*
"Murinae," Wikipedia.com, accessed Mar. 18, 2013. (Year: 2013).*
"List of sequenced bacterial genomes", Wikipedia.com; accessed Jan. 24, 2014. (Year: 2014).*
Extended European Search Report, dated Feb. 23, 2016, for corresponding European Application No. 13807796.1.
Owczarzy et al., "Predicting Stability of DNA Duplexes in Solutions Containing Magnesium and Monovalent Cations," Biochemistry, vol. 47, No. 19, 2008 (Published on Web Apr. 19, 2008), pp. 5336-5353, XP55040115.
Špringer et al., "Shielding Effect of Monovalent and Divalent Cations on Solid-Phase DNA Hybridization: Surface Plasmon Resonance Biosensor Study," Nucleic Acids Research, vol. 38, No. 20, 2010 (Published online Jul. 12, 2010), pp. 7343-7351, XP055183498.

* cited by examiner

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: capture probe
<220> FEATURE:
<221> NAME/KEY: misc_feature
<222> LOCATION: (1)..(1)
<223> OTHER INFORMATION: amino modified

<400> SEQUENCE: 1
gtcattatgt gctgccatat ctacttcaga 30

<210> SEQ ID NO 2
<211> LENGTH: 30
<212> TYPE: DNA
<213> ORGANISM: Artificial Sequence
<220> FEATURE:
<223> OTHER INFORMATION: target nucleic acid
<220> FEATURE:
<221> NAME/KEY: misc_feature
<222> LOCATION: (1)..(1)
<223> OTHER INFORMATION: biotinylated base

<400> SEQUENCE: 2
tctgaagtag atatggcagc acataatgac 30

<210> SEQ ID NO 3
<211> LENGTH: 30
<212> TYPE: DNA
<213> ORGANISM: Artificial Sequence
<220> FEATURE:
<223> OTHER INFORMATION: oligo 1

<400> SEQUENCE: 3
gtcattatgt gctgccatat ctacttcaga 30

<210> SEQ ID NO 4
<211> LENGTH: 30
<212> TYPE: DNA
<213> ORGANISM: Artificial Sequence
<220> FEATURE:
<223> OTHER INFORMATION: oligo 2

<400> SEQUENCE: 4
tctgaagtag atatggcagc acataatgac 30

METHOD FOR DETECTING NUCLEIC ACID AND NUCLEIC ACID DETECTION KIT

TECHNICAL FIELD

The present invention relates to a method for detecting a nucleic acid using hybridization between a capture probe and the nucleic acid.

BACKGROUND ART

Research by genetic information analysis of various organisms has begun, and information on a number of genes including those of human and their base sequences, and on the proteins encoded by the gene sequences and sugar chains secondarily produced from these proteins, is being rapidly clarified. Functions of biopolymers such as genes, proteins and sugar chains whose sequences were clarified can be investigated by various methods. In terms of nucleic acids, major examples of the methods include Northern blotting and Southern blotting, which can be used for investigation of various genes in relation to expression of their biological functions by utilization of various nucleic acid-nucleic acid complementarities. In terms of proteins, examples of the methods include Western blotting, which can be used for investigation of functions and expression of proteins by utilization of protein-protein reactions.

In particular, in cases where a nucleic acid of interest (target nucleic acid) is to be detected in, for example, genetic diagnosis, identification of a pathogenic bacterium or detection of a single nucleotide polymorphism, a capture probe composed of nucleic acid is employed. In recent years, simultaneous detection of a plurality of types of target nucleic acids has been carried out using a DNA chip or DNA microarray, which contains a number of capture probes immobilized on a support. More specifically, the sequence of a target nucleic acid can be investigated by bringing a capture probe immobilized on a support into contact with the target nucleic acid, and then investigating the presence or absence of hybridization between the capture probe and the target nucleic acid to test their complementarity. Examples of common methods for the hybridization of the target nucleic acid include a method in which a labeling substance is introduced into the target nucleic acid, and the resulting nucleic acid is brought into contact with the capture probe, followed by detection of a signal from the labeling substance.

There are the following methods for the introduction of the labeling substance to the target nucleic acid: a method in which the labeling substance is introduced before the hybridization with the capture probe, and a method in which the labeling substance is introduced after the hybridization. The latter method is called the post-staining method. In this method, the target nucleic acid after hybridization is brought into contact with a labeling substance to introduce the labeling substance. This method allows use of a relatively large labeling substance since the labeling substance is bound after the hybridization. Moreover, the labeling step can be repeatedly carried out for enhancing the detected signal (Patent Documents 1 and 2). It is known that, in the labeling step of the post-staining method, a labeling solution containing a monovalent metal cation such as sodium ion at a concentration of as high as about 500 to 1000 mM is used.

On the other hand, since divalent metal cations are known to be substances that activate various nucleases, their positive use in methods for detection of nucleic acid using hybridization has been avoided, and there is no known technical idea in which a divalent metal cation is used in the labeling step of the post-staining method.

PRIOR ART DOCUMENTS

Patent Documents

[Patent Document 1] JP 2011-188837 A
[Patent Document 2] JP 2003-52383 A

SUMMARY OF THE INVENTION

Problems to be Solved by the Invention

In labeling of a target nucleic acid by the post-staining method, the labeling substance that has not been introduced into the target nucleic acid needs to be removed by washing. However, as a result of testing of labeling of a target nucleic acid hybridized with a capture probe immobilized on a support by the conventional post-staining method, the present inventors discovered a problem that, during the introduction of a labeling substance into the target nucleic acid, or during the removal of the labeling substance that has not been introduced into the target nucleic acid by washing, detachment of the target nucleic acid that has once hybridized with the capture probe occurs, resulting in a low detected signal.

Although a study by the present inventors showed that the detachment of the target nucleic acid can be suppressed to some extent by sodium ion contained at a concentration of as high as about 500 to 1000 mM in a conventional labeling solution, it is still necessary, from the viewpoint of reduction of the amount of a reagent and improvement of the detection sensitivity, to find a substance that can achieve an equivalent or higher level of suppression of the detachment of the target nucleic acid even at a concentration lower than that of sodium ion.

That is, an object of the present invention is to discover a substance other than sodium ion that suppresses, in the labeling step of the post-staining method, detachment of the target nucleic acid that has once hybridized with the capture probe from the support, and to provide a nucleic acid detection method that enables detection of the target nucleic acid with a sensitivity equivalent to or higher than that achieved with sodium ion even in cases where the substance is used at a lower concentration.

Means for Solving the Problems

As a result of intensive study, the present inventors discovered that use of a solution containing a divalent metal cation, whose use in the step of hybridization of nucleic acid has been avoided, in the step of labeling of a target nucleic acid hybridized with a capture probe allows suppression of detachment of the target nucleic acid during removal of the labeling substance that has not been introduced into the target nucleic acid by washing, and that, as a result, the detected signal can be equivalent to or higher than that obtained in cases of use of sodium ion, thereby completing the present invention.

That is, the present invention is constituted by the (1) to (13) below.

(1) A method for detecting a target nucleic acid, the method comprising the steps of:

hybridizing a capture probe with a target nucleic acid to form a double-stranded nucleic acid;

bringing the formed double-stranded nucleic acid into contact with a solution containing a labeling substance and a divalent metal cation at a concentration of not less than 10 mM to introduce the labeling substance into the double-stranded nucleic acid; and detecting the labeling substance introduced into the double-stranded nucleic acid.

(2) The method according to (1), wherein the capture probe is immobilized on a support.

(3) The method according to (1) or (2), wherein the divalent metal cation is at least one selected from the group consisting of magnesium ion, zinc ion, manganese ion and calcium ion.

(4) The method according to any one of (1) to (3), wherein the concentration of the divalent metal cation in the solution is not less than 50 mM.

(5) The method according to any one of (1) to (4), wherein the labeling substance is a fluorescent substance.

(6) The method according to any one of (1) to (5), wherein the introduction of the labeling substance into the target nucleic acid is carried out using avidin-biotin interaction.

(7) The method according to (6), wherein the target nucleic acid is biotinylated and the introduction of the labeling substance is carried out by allowing interaction between labeled avidin or labeled streptavidin and biotin on the target nucleic acid.

(8) The method according to any one of (1) to (5), wherein the introduction of the labeling substance into the target nucleic acid is carried out by allowing antigen-antibody reaction between a labeled antibody or an antigen-binding fragment thereof that undergoes antigen-antibody reaction with the hybridized double-stranded nucleic acid, and the double-stranded nucleic acid.

(9) The method according to any one of (1) and (3) to (7), wherein, in the step of hybridizing the capture probe with the target nucleic acid, the capture probe is in a free state without being immobilized on a support, and the double-stranded nucleic acid formed by hybridization between the capture probe and the target nucleic acid is immobilized onto a support.

(10) The method according to (9), wherein the immobilization of the double-stranded nucleic acid onto the support is carried out by allowing antigen-antibody reaction between an antibody or an antigen-binding fragment thereof immobilized on the support, which antibody or antigen-binding fragment undergoes antigen-antibody reaction with the double-stranded nucleic acid, and the double-stranded nucleic acid.

(11) A nucleic acid detection kit comprising a capture probe and a reagent containing a divalent metal cation at a concentration of not less than 10 mM.

(12) A nucleic acid detection kit comprising a capture probe immobilized on a support and a reagent containing a divalent metal cation at a concentration of not less than 10 mM.

(13) The kit according to (11) or (12), wherein the reagent containing a divalent metal cation contains the divalent metal cation and a labeling substance.

Effect of the Invention

By the present invention, highly sensitive and reproducible detection of a target nucleic acid hybridized with a capture probe is possible.

MODE FOR CARRYING OUT THE INVENTION

Examples of the target nucleic acid to be subjected to the detection method of the present invention include, but are not limited to, genes of pathogenic bacteria and viruses, causative genes for hereditary diseases, and parts of such genes. Examples of samples containing such target nucleic acids include, but are not limited to, body fluids such as blood, serum, plasma, urine, stool, spinal fluid, saliva, swab and various tissue fluids; various tissues; paraffin-embedded samples (FFPEs) and sections thereof; and various foods and beverages, and dilutions thereof. The target nucleic acid to be used as a test substance may be a nucleic acid extracted from blood or cells by a conventional method, and DNA or RNA extracted from a sample may be used. Examples of the DNA which may be used include, but are not limited to, labeled DNAs; viral DNAs; DNAs of bacteria, molds and the like; cDNAs produced by reverse transcription of RNAs; and partial fragments thereof. Examples of the RNA which may be used include, but are not limited to, messenger RNAs (mRNAs), ribosomal RNAs (rRNAs), small RNAs, and partial fragments thereof. A chemically synthesized DNA, RNA or the like may also be used as the target nucleic acid.

As the support, a slide glass, resin substrate, membrane, bead or the like may be used. Examples of the material of the support include, but are not limited to, inorganic materials such as glass, ceramic and silicon; and polymers such as polyethylene terephthalate, cellulose acetate, polycarbonate, polystyrene, polymethylmethacrylate, silicone rubber and the like.

The capture probe means a substance that can directly and selectively bind to the target nucleic acid contained in the test sample. More specifically, in the method for detecting a target nucleic acid of the present invention, DNA, RNA, or a nucleic acid derivative such as PNA (Peptide Nucleic Acid), LNA (Locked Nucleic Acid) or ENA (Ethylene□Bridged Nucleic Acid) may be used. In cases of a nucleic acid, the derivative herein means a chemically modified derivative such as a derivative labeled with a fluorescent substance or the like, or a derivative containing a modified nucleotide (for example, a nucleotide having a halogen or a group such as alkyl including methyl; alkoxy including methoxy; thio; carboxymethyl; or the like; or a nucleotide that underwent reconstruction of the base, saturation of a double bond, deamination, replacement of an oxygen molecule with a sulfur molecule, or the like).

Since a single-stranded nucleic acid having a specific base sequence selectively binds to a single-stranded nucleic acid having the base sequence complementary to the specific base sequence or a part thereof by hybridization, the single-stranded nucleic acid having the specific base sequence corresponds to the capture probe in the present invention. The capture probe to be used in the present invention may be one commercially available, or may be obtained from living cells or the like. An especially preferred capture probe is a nucleic acid. Among nucleic acids, those having lengths of up to 200 bases, which are called oligonucleic acids, can be easily artificially synthesized using a synthesizer.

As methods of immobilization of a capture probe on a support, the following methods are known: methods in which a capture probe is synthesized on the upper surface of a support, and methods in which a preliminarily synthesized capture probe is dropped onto the upper surface of a support, and then immobilized. Examples of the methods in which a capture probe is synthesized on the upper surface of a support include the method by Ronald et al. (U.S. Pat. No. 5,705,610 B), method by Michel et al. (U.S. Pat. No. 6,142,266 B), and method by Francesco et al. (U.S. Pat. No. 7,037,659 B). Since these methods use an organic solvent for the synthesis reaction of the capture probe, the carrier is preferably a material tolerant to the organic solvent. For example, a glass support having an irregular structure prepared using the method described in Japanese Translated PCT Patent Application Laid-open No. 10-503841 may be used. Since, in particular, in the method by Francesco et al., light is radiated from the back side of the support in order to control synthesis of the capture probe, the support is preferably a material having translucency. Examples of the methods in which a capture probe is dropped onto the upper surface of a support and then immobilized include the method by Hirota et al. (JP 3922454 B), and use of a glass capillary. Examples of the glass capillary include, but are not limited to, self-made glass capillaries and commercially available products such as a micropipette (manufactured by Microsupport Co., Ltd., MP-005).

The present invention is a method for detecting a nucleic acid, comprising hybridizing a capture probe with the target nucleic acid, characterized in that the nucleic acid hybridized with the capture probe is brought into contact with a solution containing a labeling substance and a divalent metal cation to introduce the labeling substance into the hybridized nucleic acid. The hybridization step and the step of introducing the labeling body are described below.

The hybridization of the capture probe with the target nucleic acid can be carried out by a per se known method. The stringency during the hybridization of the capture probe with the target nucleic acid is known to be a function of the temperature, salt concentration, chain length of the probe, GC content of the nucleotide sequence of the probe, and the concentration of the chaotropic agent in the hybridization buffer. Examples of the conditions that may be used include those described in Sambrook, J. et al. (1998) Molecular Cloning: A Laboratory Manual (2nd ed.), Cold Spring Harbor Laboratory Press, New York. A stringent temperature condition is not less than about 30° C., and the temperature is normally about 10° C. to 70° C. Examples of other conditions include the hybridization time, concentration of the washing agent (e.g., sodium dodecyl sulfate (SDS)) and presence or absence of a carrier DNA. Various stringencies can be set by combining these conditions. Those skilled in the art may arbitrarily determine conditions for obtaining functions of the capture probe provided for detection of the desired target nucleic acid.

The hybridization of the capture probe with the target nucleic acid may be carried out in a state where the capture probe is immobilized on a support, or immobilization on the support may be carried out after the hybridization. The immobilization of the capture probe after the hybridization can be carried out by, for example, using an immobilized antibody or antigen-binding fragment (Fab fragment, $F(ab')_2$ fragment or the like) thereof that specifically binds to (undergoes antigen-antibody reaction with) the double strand formed with the target nucleic acid (see the Examples below).

The introduction of the labeling substance to the target nucleic acid hybridized with the capture probe can be carried out by a per se well-known method, and examples of the method include a method in which the target nucleic acid is brought into contact with a solution containing a labeling substance and a divalent metal cation, and the labeling substance is then introduced by a chemical reaction, enzymatic reaction, nucleic acid hybridization or the like, and a method in which a reactive functional group is introduced to the target nucleic acid by a chemical reaction, enzymatic reaction, nucleic acid hybridization or the like, and a solution containing a labeling substance and a divalent metal cation is then brought into contact with the functional group, followed by reacting the labeling substance with the functional group to achieve the introduction. For example, by introducing a nucleic acid having an amino group to the target nucleic acid by an enzymatic reaction, and then reacting the resulting nucleic acid with a labeling substance having a succinimide group that reacts with the amino group, the labeling substance can be introduced. The introduction of a labeling substance can also be carried out in a similar manner through the avidin-biotin reaction by introducing biotin to a double-stranded nucleic acid containing the target nucleic acid, and then bringing the resulting nucleic acid into contact with labeled avidin or streptavidin. Alternatively, the introduction of a labeling substance can be carried out by contacting of an intercalator-type labeling substance that is to be intercalated into the double-strand portion formed by hybridization between the target nucleic acid and the probe nucleic acid. Alternatively, the introduction of a labeling substance can be carried out by using an antibody or antigen-binding fragment (Fab fragment, $F(ab')_2$ fragment or the like) thereof that undergoes antigen-antibody reaction with a double strand (see Examples below).

Examples of labeling substances that may be used in the present invention include fluorescent substances such as organic fluorescent dyes, phosphorescent dyes, quantum dots and fluorescent proteins; radioisotopes; redox species capable of giving and receiving electrons; and substances to which an enzyme such as alkaline phosphatase or horse radish peroxidase is bound. Among these labeling substances, fluorescent substances are preferably used from the viewpoint of sensitivity and simplicity of detection.

Examples of the organic fluorescent dyes include cyanine (Cyanine 2), aminomethylcoumarin, fluorescein, indocarbocyanine (Cyanine 3), Cyanine 3.5, tetramethylrhodamine, rhodamine red, Texas red, indocarbocyanine (Cyanine 5), Cyanine 5.5, Cyanine 7, Oyster and BODIPY dyes. Examples of the intercalator-type fluorescent dyes include ethidium bromide and acridine orange, and examples of the fluorescent proteins include known fluorescent substances such as phycoerythrin (PE), allophycocyanin (APC), green fluorescent protein (GFP) and red fluorescent protein (RFP).

A luminous semiconductor particle may be used as the fluorescent substance. Examples of such a semiconductor particle include cadmium selenide (CdSe), cadmium sulfide (CdS), cadmium telluride (CdTe), Indium gallium phosphide (InGaP), chalcopyrite particles and silicon (Si). Detection of the fluorescent signal can be carried out using, for example, a fluorescence microscope or fluorescence scanner.

As described later, after the introduction of a labeling substance to the double-stranded nucleic acid, the labeling substance that has not been introduced into the double-stranded nucleic acid needs to be removed by washing. From the viewpoint of increasing the detection sensitivity, it is important to suppress, during the removal of the labeling substance by washing, detachment the target nucleic acid from the double-stranded nucleic acid to which the labeling substance was introduced. In the present invention, by introduction of a labeling substance using a solution containing the labeling substance and a divalent metal cation, the detachment of the target nucleic acid during removal of the labeling substance by washing can be remarkably suppressed.

The divalent metal cation means an element/complex that can release two electrons to become a divalent cation in a solution. Examples of the divalent metal cation include alkaline earth metal ions such as beryllium ion, magnesium ion, calcium ion, strontium ion, barium ion and radium ion; monatomic ions composed of a transition metal, such as manganese ion, cobalt ion and zinc ion; and complex ions such as thiocyanoiron (III) ion, tetraamminezinc (II) ion and hexaamminenickel (II) ion. In particular, in consideration of solubility in water and the environmental load, the divalent metal cation is preferably at least one selected from the group consisting of magnesium ion, zinc ion, manganese ion and calcium ion. In consideration of stability of binding to a double-stranded nucleic acid, the divalent metal cation is especially preferably magnesium ion and/or manganese ion.

The concentration of the divalent metal cation in the solution is not less than 10 mM. The concentration is preferably not less than 50 mM, more preferably not less than 100 mM in view of strength of the detected signal of nucleic acid. The concentration is preferably less than 500 mM from the viewpoint of reducing the amount of a reagent and preventing an increase in the noise due to precipitation of the metal cation in the solution.

Subsequently, the labeling substance that has not been introduced into the double-stranded nucleic acid is preferably removed by washing. The step of removal itself by washing can be carried out by a per se well-known method. For example, the washing may be carried out using, as a washing liquid, a buffer (e.g., citrate buffer such as SSC) containing a surfactant (preferably, nonionic surfactant such as Tween (trade name)), normally at a temperature 3° C. to 10° C. lower than the temperature for the hybridization, for 1 minute to 10 minutes.

Subsequently, the labeling substance introduced into the double-stranded nucleic acid is detected. The detection step itself can be carried out by a well-known method, and is possible by detection of a signal from the labeling substance introduced into the double-stranded nucleic acid. The detected signal is compared with the noise in the vicinity. More specifically, the signal value obtained for the position where the capture probe is immobilized is compared with the signal value obtained for another position, and, in cases where the former value is higher, the target nucleic acid is considered to be detected. The measurement of the signal value can be carried out by a well-known method for each label. Since a variety of devices for the measurement are commercially available, the measurement can be easily carried out using a commercially available measuring device. For example, in cases where the label is a fluorescent label, the measurement can be easily carried out using a commercially available DNA chip scanner or the like. In some cases, quantification of the target nucleic acid is also possible by measurement of the signal value. Since quantification of the target nucleic acid inevitably accompanies detection of the target nucleic acid, the quantification of the target nucleic acid is also included in the detection method of the present invention.

Preferred modes of the nucleic acid detection kit of the present invention is described below. The nucleic acid detection kit of the present invention at least comprises a capture probe and a reagent containing a divalent metal cation. The reagent containing a divalent metal cation is preferably a reagent containing the divalent metal cation and a labeling substance. The capture probe may be immobilized on a support. The support on which the capture probe of the present is immobilized, contained in the detection kit of the present invention, is prepared by immobilization of the capture probe on the support. The reagent containing a divalent metal cation included in the kit of the present invention may be either in the dry state or in the solution state, and, in cases where the reagent is in the dry state, the kit may contain a solvent to dissolve the reagent. Other examples of reagents that may be contained in the detection kit of the present invention include a reagent containing the labeling substance, reagent for pH adjustment, surfactant, and a reagent containing protein or nucleic acid for prevention of adsorption of the labeling substance to the support. These reagents may be either in the dry state or in the solution state, and may be either separate reagents or arbitrarily mixed reagents. In cases where a reagent is in the dry state, the kit may contain a solvent to dissolve the reagent.

The present invention is described in more detail by way of Examples below. However, the technical scope of the present invention is not limited by these Examples.

Example 1

(1) Preparation of DNA Chip

As a capture probe, an oligo DNA modified with an amino group at the 5'-end was prepared by custom synthesis by Operon Biotechnologies. Table 1 shows the base sequence of the capture probe. This capture probe was immobilized on a "3D-Gene" substrate (256-column substrate), manufactured by Toray Industries, Inc., to provide a DNA chip for evaluation.

(2) Preparation of Target Nucleic Acid

As a target nucleic acid, a 30-base oligo DNA having the complementary sequence of the capture probe, which oligo DNA has biotin introduced at the 5'-end (Table 1), was prepared by custom synthesis by Operon Biotechnologies. Table 1 shows the base sequence of the target nucleic acid. The oligo DNA was diluted to a concentration of 200 fmol/l with 1× hybridization solution (described later), to provide a sample DNA.

TABLE 1

| | Probe sequence 5'->3' | |
|---|---|---|
| Capture probe | GTCATTATGT GCTGCCATAT CTACTTCAGA (SEQ ID NO: 1) | 5'-end aminated |
| Target nucleic acid | TCTGAAGTAG ATATGGCAGC ACATAATGAC (SEQ ID NO: 2) | 5'-end biotinylated |

(3) Hybridization

To 5 μl of the sample DNA, 35 μl of 1× hybridization solution (1 wt % BSA (bovine serum albumin), 5×SSC, 1 wt % SDS (sodium dodecyl sulfate), 50 ng/ml salmon sperm DNA solution, 5 wt % dextran sulfate sodium, 30% formamide) was added, to provide a hybridization solution. The whole solution was injected into the DNA chip, and the chip was then placed in an incubator warmed at 32° C. Hybridization was performed according to the standard protocol for "3D-gene", with stirring by rotation at 250 rpm at 32° C. for 2 hours. Thereafter, the DNA chip was washed for 5 minutes with a washing liquid (0.5×SSC, 0.1 wt % SDS (sodium dodecyl sulfate)) warmed at 30° C., and dried using a spin drier (Wakenyaku Co., Ltd.).

As the divalent metal cation to be added for labeling of the sample DNA, magnesium ion was added. To a fluorescent substance-containing buffer for labeling of the sample DNA (50 ng/μl SAPE (streptavidin-phycoerythrin, Prozyme, Inc.), 100 mM MES (2-morpholinoethanesulfonic acid sodium salt), 0.05 wt % TWEEN® 20 (trade name), 2 mg/ml BSA (bovine serum albumin)), 1 M magnesium chloride hexahydrate was added such that the final concentration of magnesium ion was adjusted to 10, 20, 50, 100, 200, 300 or 500 mM, to provide labeling solutions. The concentration of MES-derived sodium ion was 74 mM. Each labeling solution was dropped onto the DNA chip, and the chip was then incubated at 35° C. for 5 minutes. The chip was then washed for 5 minutes with a washing liquid (6×SSPE buffer, 0.01 wt % TWEEN® 20 (trade name)) warmed at 30° C., and then dried using a spin drier (Wakenyaku Co., Ltd.). The DNA chip after labeling was subjected to detection of fluorescence signals using a DNA chip scanner (manufactured by Toray Industries, Inc.). In terms of setting of the scanner, the laser output was 100%, and the photomultiplier voltage was set to 70%.

Comparative Example 1

No divalent metal cation was added for the labeling of the sample DNA, and the fluorescent substance-containing buffer for labeling of the sample DNA (50 ng/μl SAPE (streptavidin-phycoerythrin, Prozyme, Inc.), 100 mM MES (2-morpholinoethanesulfonic acid sodium salt), 0.05 wt % TWEEN® 20 (trade name), 2 mg/ml BSA (bovine serum albumin)) was used as it is as the labeling solution. The concentration of MES-derived sodium ion was 74 mM. The labeling solution was dropped onto the DNA chip, and the chip was then incubated at 35° C. for 5 minutes. The chip was then washed for 5 minutes with the washing liquid (6×SSPE buffer, 0.01 wt % TWEEN® 20 (trade name)) warmed at 30° C., and then dried using a spin drier (Wakenyaku Co., Ltd.), followed by detection of a fluorescence signal under the same conditions as in Example 1.

Reference Example 1

Predetermined amounts of sodium chloride were added to the fluorescent substance-containing buffer (50 ng/μl SAPE (streptavidin-phycoerythrin, Prozyme, Inc.), 100 mM MES (2-morpholinoethanesulfonic acid sodium salt), 0.05 wt % TWEEN® 20 (trade name), 2 mg/ml BSA (bovine serum albumin)), to provide solutions. The preparation of the solutions was carried out such that the final concentration of sodium ion was adjusted to 500 or 1000 mM, to provide labeling solutions. Each labeling solution was dropped onto the DNA chip, and the chip was then incubated at 35° C. for 5 minutes. The chip was then washed for 5 minutes with the washing liquid (6×SSPE buffer, 0.01 wt % TWEEN® 20 (trade name)) warmed at 30° C., and then dried using a spin drier (Wakenyaku Co., Ltd.), followed by detection of fluorescence signals under the same conditions as in Example 1.

The results of Example 1, Comparative Example 1 and Reference Example 1 are shown in Table 2. From the results of Example 1 and Comparative Example 1, it was found that the detected signal was improved by the inclusion of magnesium ion to the reagent for labeling of the sample DNA. In addition, from the results of Example 1 and Reference Example 1, it was found that, in the cases where magnesium ion was added to the reagent for labeling of the sample DNA, the detected signal was equivalent to, or higher than, the signals detected in the cases of addition of sodium ion even at a magnesium ion concentration lower than that of sodium ion, and that the detected signal was largely improved in the cases where the magnesium ion concentration was not less than 50 mM. The detected signal at a spot where the capture probe was not immobilized (noise) was 230 to 270.

TABLE 2

| Cation type | | | | Magnesium | | | | | Sodium | |
|---|---|---|---|---|---|---|---|---|---|---|
| Cation concentration (mM) | 0 | 10 | 20 | 50 | 100 | 200 | 300 | 500 | 500 | 1000 |
| Signal intensity | 971 | 1462 | 1646 | 2334 | 2812 | 2705 | 2936 | 2726 | 1563 | 1685 |
| | Comparative Example 1 | | | | Example 1 | | | | Reference Example 1 | |

Reference Example 2

(1) Measurement of Melting Temperature (Tm) of Double-Stranded DNA

As a possible mechanism of the improvement of the detected signal by addition of the divalent metal cation in labeling of the sample DNA, an increase in stability of the double-stranded DNA formed by hybridization between the capture probe and the sample DNA merely due to an increased salt concentration during the hybridization could be expected—that is, the possibility that the improvement was merely due to an increased Tm was expected. In view of this, in order to evaluate stability of the double strand of the double-stranded DNA in the presence of a cation, Tm of the double-stranded DNA was measured at various cation concentrations.

The following solutions were prepared for the measurement of Tm: solutions prepared by adding 1 M magnesium chloride hexahydrate to 500 μl of 100 mM MES such that the final concentration of magnesium ion was adjusted to 0, 10, 20, 50, 100, 200, 300 or 500 mM; 100 mM MES itself; and solutions prepared by adding 5 M sodium chloride to 500 μl of 100 mM MES such that the final concentration of sodium ion was adjusted to 500 or 1000 mM. To each of the solutions for the measurement of Tm, 1 mM Oligo 1 and Oligo 2, which are the synthetic DNAs shown in Table 3 (Oligo 1 and Oligo 2 have complementary sequences), were added to a final concentration of 2 μM, to allow formation of double-stranded DNA. Tm of the double-stranded DNA in the assay solution was measured using a Tm analysis system (manufactured by Shimadzu Corporation, TMSPC-8) and an ultraviolet/visible/near-infrared spectrophotometer (manufactured by Shimadzu Corporation, UV-1650PC), and data obtained by measurement using an 8-position micro multicell (optical path, 10 mm) (temperature measurement range, 20 to 95° C.; heating rate, 1.0° C./min.) were subjected to analysis software (manufactured by Shimadzu Corporation, Lab Solution) to determine Tm by integration.

TABLE 3

| | Probe sequence 5'->3' |
|---|---|
| Oligo 1 | GTCATTATGT GCTGCCATAT CTACTTCAGA (SEQ ID NO: 3) |
| Oligo 2 | TCTGAAGTAG ATATGGCAGC ACATAATGAC (SEQ ID NO: 4) |

The results of measurement of Tm at the various cation concentrations are shown in Table 4. Based on the results, Tm was higher in the cases where magnesium ion was added than in the cases where magnesium ion was not added. However, Tm hardly varied among the cases where the magnesium ion concentration was not less than 10 mM, and, also in the cases where sodium ion was added at 500 mM or 1000 mM, Tm was equivalent to those observed in the cases where magnesium ion was added at not less than 10 mM. That is, it was found that, although addition of a divalent metal cation increases the Tm value of a double-stranded DNA to some extent, the increase in the Tm value does not contribute to improvement of the detected signal.

TABLE 4

| Cation type | Magnesium | | | | | | | | Sodium | |
|---|---|---|---|---|---|---|---|---|---|---|
| Cation concentration (mM) | 0 | 10 | 20 | 50 | 100 | 200 | 300 | 500 | 500 | 1000 |
| Melting temperature (Tm, ° C.) | 63.5 | 72.4 | 73.5 | 73.3 | 73.6 | 73.4 | 73.2 | 73.6 | 73.4 | 74.1 |
| | Reference Example 2 | | | | | | | | | |

Example 2

As the divalent metal cation to be added for labeling of the sample DNA, calcium ion, manganese ion or zinc ion was added. To the fluorescent substance-containing buffer (50 ng/μl SAPE (streptavidin-phycoerythrin, Prozyme, Inc.), 100 mM MES (2-morpholinoethanesulfonic acid sodium salt), 0.05 wt % TWEEN® 20 (trade name), 2 mg/ml BSA (bovine serum albumin)), 1 M calcium chloride dihydrate, 1 M aqueous manganese chloride solution and 1 M aqueous zinc chloride solution were added such that the final concentration of each of calcium ion and manganese ion was adjusted to 100 or 500 mM, to provide labeling solutions. Each labeling solution was dropped onto the DNA chip, and the chip was then incubated at 35° C. for 5 minutes. The chip was then washed for 5 minutes with the washing liquid (6×SSPE buffer, 0.01 wt % TWEEN® 20 (trade name)) warmed at 30° C., and then dried using a spin drier (Wakenyaku Co., Ltd.), followed by detection of fluorescence signals under the same conditions as in Example 1.

The detection results are shown in Table 5. Similarly to the cases where magnesium ion was added in Example 1, higher signals were detected in the cases where calcium ion or manganese ion was added than in the cases where no divalent metal cation was added (Comparative Example 1). The signal was also remarkably improved compared to the cases where sodium ion was added at a concentration of 500 or 1000 mM in Reference Example 1. The detected signal at a spot where the capture probe was not immobilized (noise) was 230 to 270.

TABLE 5

| Cation type | | Magnesium | Calcium | | Manganese | Zinc | Sodium | |
|---|---|---|---|---|---|---|---|---|
| Cation concentration (mM) | 0 | 100 | 100 | 500 | 100 | 100 | 500 | 1000 |
| Signal intensity | 971 | 2812 | 1866 | 2650 | 2757 | 2786 | 1563 | 1685 |
| | Comparative Example 1 | Example 1 | Example 2 | Example 2 | Example 2 | Example 2 | Reference Example 1 | |

Example 3

In the present Example, variation in the detected signal due to addition of a divalent metal cation was studied. As the divalent metal cation to be added for labeling of the sample DNA, manganese ion was added. To the fluorescent substance-containing buffer for labeling of the sample DNA (50 ng/μl SAPE (streptavidin-phycoerythrin, Prozyme, Inc.), 100 mM MES (2-morpholinoethanesulfonic acid sodium salt), 0.05 wt % TWEEN® 20 (trade name), 2 mg/ml BSA (bovine serum albumin)), 1 M magnesium chloride hexahydrate was added such that the final concentration of magnesium ion was adjusted to 100 mM, to provide labeling solutions. The concentration of MES-derived sodium ion was 74 mM. Each labeling solution was dropped onto the DNA chip, and the chip was then incubated at 35° C. for 5 minutes. The chip was then washed for 5 minutes with the washing liquid (6×SSPE buffer, 0.01 wt % TWEEN® 20 (trade name)) warmed at 30° C., and then dried using a spin drier (Wakenyaku Co., Ltd.). The DNA chip after labeling was subjected to detection of fluorescence signals using a DNA chip scanner (manufactured by Toray Industries, Inc.). In terms of setting of the scanner, the laser output was 100%, and the photomultiplier voltage was set to 70%. The CV value, which is an index of variation of the detected signals in the DNA chip, is shown in Table 6. The CV value was calculated as follows: (standard deviation for 4 spots)/(mean signal value for 4 spots)×100.

Comparative Example 3

In the same manner as in Comparative Example 1, hybridization and labeling of the sample DNA were carried out. The CV value, which is an index of variation of the detected signals in the DNA chip, is shown in Table 6. The CV value was calculated in the same manner as in Example 3.

Reference Example 3

A predetermined amount of sodium chloride was added to the fluorescent substance-containing buffer (50 ng/μl SAPE (streptavidin-phycoerythrin, Prozyme, Inc.), 100 mM MES (2-morpholinoethanesulfonic acid sodium salt), 0.05 wt %

TWEEN® 20 (trade name), 2 mg/ml BSA (bovine serum albumin)), to provide a solution. The preparation of the solution was carried out such that the final concentration of sodium ion was adjusted to 1000 mM, to provide a labeling solution. The labeling solution was dropped onto the DNA chip, and the chip was then incubated at 35° C. for 5 minutes. The chip was then washed for 5 minutes with the washing liquid (6×SSPE buffer, 0.01 wt % TWEEN® 20 (trade name)) warmed at 30° C., and then dried using a spin drier (Wakenyaku Co., Ltd.), followed by detection of fluorescence signals under the same conditions as in Example 1. The CV value, which is an index of variation of the detected signals in the DNA chip, is shown in Table 6. The CV value was calculated in the same manner as in Example 3.

From Table 6, it was shown that the CV value was remarkably improved in the case where magnesium was added at 100 mM compared to the cases where magnesium was not added or sodium was added at 1000 mM. That is, variation among spots was improved.

TABLE 6

| Cation type | Sodium | Magnesium | |
|---|---|---|---|
| Cation concentration (mM) | 1000 | 0 | 100 |
| CV value | 11.0 | 11.9 | 3.3 |
| | Reference Example 3 | Comparative Example 3 | Example 3 |

Example 4, Comparative Example 4

In the present Example, a study was carried out to see whether detection sensitivity can be increased by addition of magnesium chloride to Detection Reagent 1, which is to be used for labeling of a DNA-RNA double strand formed by hybridization between a capture probe not immobilized on a support and a target nucleic acid. Hybrid Capture 2 (trade name; QIAGEN), which detects HPV (human papilloma virus) by allowing formation of a DNA-RNA double strand, was used to study the effect of the present invention. The principle of Hybrid Capture 2 (trade name) is as follows. DNA of HPV is allowed to hybridize with its complementary RNA, and an antibody that recognizes a DNA-RNA double strand is then used to capture the resulting hybrid on a substrate. By further binding an antibody that recognizes the labeled DNA-RNA double strand thereto, labeling and detection of HPV DNA is achieved. A test was carried out to see whether the detection sensitivity is increased by addition of a magnesium chloride solution for the labeling reaction. The reaction with Hybrid Capture 2 (trade name) was carried out according to the instructions attached to the product.

(1) Preparation of Sample

For the sample DNA, a recombinant plasmid pHPV16, which contains a cloned genomic DNA of human papillomavirus, was purchased from Health Science Research Resources Bank, and used. The total length of pHPV16 was 16,600 base pairs. To each of a sample solution prepared such that pHPV16 was contained at 1 amol, and a sample solution prepared such that pHPV16 was contained at 0.01 amol, 25 µl of a sample extraction reagent was added. The resulting mixture was stirred using a vortex mixer, and the reaction was then allowed to proceed in a water bath at 65° C. for 45 minutes.

(2) Hybridization

To 25 µl of a probe solution prepared according to the instructions, 75 µl of the sample was added, and the resulting mixture was stirred by shaking using a rotary shaker (1100 rpm) for about 3 minutes. Thereafter, the reaction was allowed to proceed in a hybridization oven at 65° C. for 60 minutes.

(3) Hybrid Capture (Trade Name)

To a well of a capture plate, 100 µl of the hybridization reaction solution was transferred, and the reaction was allowed to proceed with shaking using a rotary shaker (1100 rpm) at 25° C. for 60 minutes. Thereafter, the supernatant was removed.

Detection Reaction

After aliquoting Detection Reagent 1 (alkaline phosphatase-labeled mouse anti-DNA-RNA complex monoclonal antibody) in 75-µl volumes into the wells, the reaction was allowed to proceed at 25° C. for 30 minutes. At this time, Detection Reagent 1 supplemented with magnesium chloride at a final concentration of 100 mM (Mg-containing reagent) and Detection Reagent 1 to which magnesium chloride was not added (Mg-free reagent) were provided, and each of these was used for the reaction. Thereafter, the wells were washed with a washing liquid, and Detection Reagent 2 (disodium 2-chloro-5-(4-methoxyspiro{1,2-dioxethane-3,2'-(5'-chloro)tricycle[3.3.11]decan}-4-yl)-1-phenyl phosphatase solution) was added thereto, followed by allowing the reaction to proceed at 25° C. for 15 minutes. Thereafter, the amount of luminescence was measured using a luminometer. The detection results are shown in Table 7.

As a result, it was found that the addition of magnesium improved the luminescence signal compared to the cases where magnesium was not added. The luminescence signal of the negative control that was subjected to the measurement at the same time was 3730. Thus, it was shown that, in the detection reaction using Hybrid Capture 2 (trade name), addition of magnesium is effective for improvement of the sensitivity.

TABLE 7

| Cation type | Magnesium | |
|---|---|---|
| Cation concentration (mM) | 100 | 0 |
| Luminescence signal (1amol) | 538054 | 376951 |
| Luminescence signal (0.01amol) | 8547 | 7192 |
| | Example 4 | Comparative Example 4 |

INDUSTRIAL APPLICABILITY

The present invention can be used for genetic diagnosis, identification of a pathogenic bacterium, or nucleic acid detection such as detection of a single nucleotide polymorphism.

The invention claimed is:

1. A method for detecting a target nucleic acid by a DNA chip, said method comprising the steps of:

(A) obtaining a capture probe configured for a DNA chip detection method and having complementarity to hybridize with a target nucleic acid, said target nucleic acid also configured for a DNA chip detection method, wherein said capture probe is immobilized on the DNA chip surface formed from glass, resin substrate or membrane, (B) hybridizing the capture probe, in a hybridization solution configured for a DNA chip detection method, with the target nucleic acid to form a double-stranded nucleic acid connected to the DNA chip by way of the capture probes connection to the DNA chip surface;

(C) bringing said formed double-stranded nucleic acid into contact with a labeling solution to bond a labeling substance with said double-stranded nucleic acid, wherein the labeling solution is configured for a DNA chip detection method and contains:

(1) the labeling substance consisting of a fluorescent substance; and (2) a divalent metal cation of magnesium ion, zinc ion, or calcium ion at a concentration of 100 mM to 500 mM;

(D) removing the portion of the labeling substance that was not bonded with the double-stranded nucleic acid in step (C) by washing the DNA chip with the with a washing liquid configured for a DNA chip detection method; and (E) detecting said labeling substance bonded with the double-stranded nucleic acid by a DNA chip scanner.

2. A method for detecting a target nucleic acid by a DNA chip, said method comprising the steps of:

(A) obtaining a capture probe configured for a DNA chip detection method and having complementarity to hybridize with a biotinylated target nucleic acid, said biotinylated target nucleic acid also configured for a DNA chip detection method, wherein said capture probe is immobilized on the DNA chip surface formed from glass, resin substrate or membrane, (B) hybridizing the capture probe, in a hybridization solution configured for a DNA chip detection method, with the biotinylated target nucleic acid to form a double-stranded nucleic acid connected to the DNA chip by way of the capture probes connection to the DNA chip surface;

(C) bringing said formed double-stranded nucleic acid into contact with a labeling solution to bond a labeling substance with said double-stranded nucleic acid via a streptavidin-biotin interaction, wherein the labeling solution is configured for a DNA chip detection method and contains:

(1) the labeling substance consisting of streptavidin coupled to a fluorescent substance; and (2) a divalent metal cation of magnesium ion, zinc ion, or calcium ion at a concentration of 100 mM to 500 mM;

(D) removing the portion of the labeling substance that was not bonded with the double-stranded nucleic acid in step (C) by washing the DNA chip with a washing liquid configured for a DNA chip detection method; and (E) detecting said labeling substance bonded with the double-stranded nucleic acid by a DNA chip scanner.

3. A method for detecting a target nucleic acid by a DNA chip, said method comprising the steps of:

(A) obtaining a capture probe configured for a DNA chip detection method and having complementarity to hybridize with a target nucleic acid, said target nucleic acid also configured for a DNA chip detection method, wherein said capture probe is immobilized on the DNA chip surface formed from glass, resin substrate or membrane, (B) hybridizing the capture probe, in a hybridization solution configured for a DNA chip detection method, with the target nucleic acid to form a double-stranded nucleic acid connected to the DNA chip by way of the capture probes connection to the DNA chip surface;

(C) bringing said formed double-stranded nucleic acid into contact with a labeling solution to bond a labeling substance with said double-stranded nucleic acid, wherein the labeling solution is configured for a DNA chip detection method and contains:

(1) the labeling substance consisting of a fluorescent substance; and (2) a divalent metal cation of magnesium ion at a concentration of 100 mM to 500 mM;

(D) removing the portion of the labeling substance that was not bonded with the double-stranded nucleic acid in step (C) by washing the DNA chip with a washing liquid configured for a DNA chip detection method;

and (E) detecting said labeling substance bonded with the double-stranded nucleic acid by a DNA chip scanner.

* * * * *